(12) United States Patent
Palladino et al.

(10) Patent No.: US 6,348,965 B1
(45) Date of Patent: Feb. 19, 2002

(54) SOLID STATE FLUORESCENCE AND ABSORPTION SPECTROSCOPY

(76) Inventors: Henry Palladino; Andrew Hood, 666 E. 233rd St., both of Bronx, NY (US) 10466

( * ) Notice: Subject to any disclaimer, the term of this patent is extended or adjusted under 35 U.S.C. 154(b) by 0 days.

(21) Appl. No.: 09/404,968

(22) Filed: Sep. 24, 1999

(51) Int. Cl.[7] .................................................. G01J 1/10
(52) U.S. Cl. .................................................. 356/243.1
(58) Field of Search .......................... 356/301, 243.1, 356/243.4, 243.8

(56) References Cited

U.S. PATENT DOCUMENTS

| | | | |
|---|---|---|---|
| 5,861,256 A | * | 1/1999 | Glass et al. ........................ 435/6 |
| 5,870,188 A | * | 2/1999 | Ozaki et al. ..................... 356/301 |
| 5,973,782 A | * | 10/1999 | Bomse ........................ 356/346 |
| 5,991,031 A | * | 11/1999 | Higashi ........................ 356/346 |
| 6,078,388 A | * | 6/2000 | Njamfa ........................ 356/300 |
| 6,236,456 B1 | * | 5/2001 | Giebeler et al. ............. 356/318 |

* cited by examiner

*Primary Examiner*—Frank G. Font
*Assistant Examiner*—Michael P. Stafira
(74) *Attorney, Agent, or Firm*—Ward & Olivo

(57) ABSTRACT

Solid state devise for the calibration of microplate fluorescence and absorption readers and spectrometers is described. When present in a single moiety, the disclosed device can tell if the lamp photomultiplier tube and optical alignment of the microplate reader or spectrometer deviates from its true value. When present as graded calibration pieces, the disclosed device can be used to calibrate a fluorescence or absorption reader. Calibration pieces are shaped, polished and coated with color absorbing or fluorescent standard to fit in microplate holding trays or spectrometers which are commercially available. Solid state devices are stable and durable and very inert to manipulations and thus are more reliable and unfaltering than solutions for absorption and fluorescence microplate readers or spectrometers.

17 Claims, 5 Drawing Sheets

SOLID STATE FLUORESCENCE AND ABSORPTION SPECTROSCOPY

TECHNICAL FIELD OF THE INVENTION

This invention relates to fluorescence and absorption spectroscopy using solid state standard coatings on optical glass or quartz. More specifically it relates to the calibration of fluorescence or absorbance reading microplate readers or spectrometers using a solid state device invention which is shaped to fit into square or bullet shaped microplate holders or spectrometer chambers and are read on appropriate fluorescence or absorption readers.

BACKGROUND OF THE INVENTION

Standards which validate true capacity and integrity of various measuring devices are well known in the art. Whether standards used are solid, gas or liquid samples, they are quite common among all testing machines. The purpose of standards is to make sure that testing equipment is reading accurately, so that the measurements obtained on unknown quantities can be accepted as true and reliable. For this reason all testing machines have some standard that uniformly performs calibrations to assure readings which are consistent with the samples used and the unknowns tested. Traditionally this has required many samples of the materials at various compositions used as controls.

Spectroscopy is used to identify various unknown substances by reading spectroscopic patterns. Usually samples are tested over a wide range of wavelengths, from the Ultra Violet to Visible to Infra-Red bands of the spectrum. Testing relies on the consistent absorption or fluorescence by various compounds at specific wavelengths of light which produce a consistent pattern identifying the substance. Sometimes making an accurate identification of a substance is difficult because it is entirely dependent on absorption values of the substance. With fluorescent spectroscopy the user can examine the absorption or excitation of the compound as well as its emission of energy in the form of light as it returns to the ground state. For these substances, there are now two readings, which make it possible to identify unknowns with greater precision than ever before. To produce more accurate readings, solid state standards in microplates of any number can be made that standardize testing so that readings can be relied upon quickly and uniformly. The compounds absorb light during excitation and emit light of longer wavelength during emission. Furthermore, fluorescence spectroscopy is much more sensitive than U.V., visible or infra-red spectroscopy. This is because fluorescence is the excitation of the compound to a glow. This fluorescent glow can also be amplified to extremes by increasing voltage to the photomultiplier tube.

A review of the patent literature shows that the use of solid state standards with coatings in the calibration of microplate readers is a novel idea and not covered in the patent literature. For example, U.S. Pat. No. 4,661,711 uses an internal standard consisting of a fiberoptic bundle which fluoresces to calibrate a detector after splitting a light beam. The standard presented herein is an external optical glass moiety shaped to fit within a microplate holder or spectrometer chamber which is read in the corresponding instrument. The coated insert when read, gives a non changing reading provided that the photomultiplier (detector), voltage to the photomultiplier tube, lamp light output, monochomator if present and internal electronics do not change over time.

U.S. Pat. No. 5,414,258 entitled "Apparatus and method for calibration of fluorescence", describes an apparatus for reading the non visible fluorescence intensity of bar code shaped fluorescent targets which can be adjusted in the apparatus by changing the distance between the target and the detector or by changing the area of the target exposed to the detector. The solid state standards of the present invention can be used in absorption spectroscopy as well as fluorescence spectroscopy, and are shaped to fit microplate wells not as bar codes. The distance to the photomultiplier tubes is constant when reading these solid state standards in microplate readers although voltages applied to the photomultiplier tube (gain), will decrease or increase the relative magnitude of the fluorescence detected.

U.S. Pat. No. 3,854,050 entitled "High precision fluorometer for measuring enzymatic substrates in tissue" uses a fluorescent glass in combination with attenuating filters in a custom cuvette standard. The present invention however describes a microplate reader which uses absorbance or fluorescence standards on coated glass or quartz contoured to fit in a microplate or spectrometer; in contrast to the macro-cuvette holding apparatus described in the '050 patent which employs a rectangular cuvette shaped reference. Instead of using attenuating filters to delimit the fluorescent emission of a specific reference standard, the invention disclosed herein uses industrial coatings which absorb in the Ultra Violet, Visible or Infra-Red electromagnetic ranges and are stable over time.

U.S. Pat. No. 5,503,910, entitled "Organic electroluminescence device", describes an organic electroluminescence device consisting of a transparent anode (negatively charged electrode) which is coated with two layers of organic. When an electric field is applied, the first organic layer emits light at 380–480 nm, the second layer emits light at 480–580 nm and an organic in the first and second layer emits light at 580–620 nm. Overall the effect of this device is the emission of high energy white light. Alternatively in the present invention the reference standards emit monochromatic light when exposed to light delivered through an excitation or absorbance filter and are not dependant upon an electric field to emit light. More tellingly the samples or standards are coated with fluorescent or absorptive substances rather than an anode.

U.S. Pat. No. 4,868,126 entitled "Method of calibrating a fluorescent microscope using fluorescent calibration microbeads simulating stained cells" uses a hydrophilic microbead which covalently binds to a fluorescent molecule and can be visualized under a fluorescence microscope. The beads are microscopic (ranging from 1–20 microns) and therefore scatter light, which may be a limiting factor in a quantitative measurement device such as a microplate reader. Another problem with the microbeads-fluorescent molecule covalent bond is their lack of stability in solution. The coatings in the present invention are baked at 250 degrees Centigrade for several days by spectral coating experts resulting in a stable microwell insert.

U.S. Pat. No. 5,689,110 entitled "Calibration method and apparatus for optical scanner", uses a beam splitter in a fluorescence spectrometer to compare two internal solid state standards, a calibration ruby and a gold standard. Neither of these standards are among the coatings which are utilized by the invention disclosed herein and moreover the standards are external to the measurement device. Furthermore a ratio method similar to the one described by the '110 patent could not be used in a microplate reader.

U.S. Pat. No. 4,925,629 discloses a diagnostic device for preparing a standard calibration curve which employs a set of liquid standard tubes of diluted liquids which serve as a reservoir of connecting tubes. A micropipetting device then simultaneously draws up solution from eight tubes for serial transfer to other tubes. In contrast to the use of liquid as a standard, the present invention uses microplate pellets independently placed within the microplate and may be coated with known fluorescent or calorimetric substances. Another difference between the present invention and that of the '169 patent is that due to evaporation, standards in a liquid state will decrease in volume and become more concentrated over time producing erroneous readings. The standards described herein are permanently fashioned to have a fixed pathlength. The microplate pellets disclosed herein are independently absorbing or fluorescent pieces so that they may be read and reread without further dilutional manipulation or transfer between plates.

Patent abstracts of Japan 01-142440 entitled "Cuvette holder for automated chemical analysis" discloses the use of colored glass filters to calibrate a spectrophotometer. The solid state standards of the present invention are optical glass but are coated with absorbance or fluorescent constituents and is not simply using colored glass filters for calibration.

Patent abstracts of Japan No. 07-10594 entitled "Optical Glass Filter for Calibrating Transmisivity or Absorbance" describes the use of optical glass for calibration purposes. These band pass filters are composed of S10<SB>2/SB>, alkali metal oxide and doping agents to vary the composition of the glass. The solid state microplate pellets of the present invention are optical glass but are coated with absorbance or fluorescent constituents which are not acting as band pass filters even though both inventions may read in the 300–700 nm range.

Patent abstracts of Japan No. 55-129728 employs a polished glass cell for use in a turbometric measuring devise. Although optical glass is used as a measuring cell, these polished cells are not or could not be used as a microplate insert and are not intended to be read in an absorbance or fluorescence type reader.

U.S. Pat. No. 5,582,168 describes the general measurement of fluorescence or turbidity in human tissue. Reflectance or fluorescence using a reflection of electromagnetic information is fundamentally different from measuring microsamples in an absorbance or fluorescence microplate reader. Moreover the '168 patent does not use glass microplate pellets in its examination of the lens of the eye.

U.S. Pat. No. 4,971,439 entitled "The Wavelength Calibration Method and Apparatus" is discussed next. The setting of the monochromator to obtain 'zero order light' is done using a didyminium glass filter. As noted in the patent the first absorption of the glass filter occurs at a wavelength of 585.5 nm. The optical glass used in the present invention's microplate pellets are not didyminium. Although microplate readers may have monochromators, this invention checks the monochromator as well as the excitation lamp and the photomultiplier tube by giving a constantly absorbing coating on the microplate pellet.

U.S. Pat. No. 4,135,816 entitled "Method and Application for Determining the Total Protein Content or Individual Amino Acids" uses a fluorometric method to examine the fluorescence and autofluorescence of a semi-solid suspension of protein and amino acids. We use coatings on microplate pellets to standardize the absorbance or fluorescence readings of microplate readers.

Accordingly it is desirable to have a method and apparatus for the calibration of fluorescence or absorbance reading microplate readers or spectrometers using a solid state device which is shaped to fit into square or bullet shaped microplate holders or spectrometer chambers and are read on appropriate fluorescence or absorption readers.

SUMMARY OF THE INVENTION

Infra-red and fluorescence microscopy employ analysis of the electromagnetic spectrum by using an excitation source such as a lamp, (deuterium, xenon, quartz, halogen or infra-red) that excites compounds to an excited state followed by their return to the original ground state. This condition allows for two readings in fluorescence measurement as opposed to one reading in the spectroscopic analysis. The return to the ground state in U.V., visible and infra-red is instantaneous ($1 \times 10^{-20}$ to $1 \times 10^{-17}$ sec), while with fluorescence it takes a circuitous route before returning to the ground state ($1 \times 10^{-14}$ to $1 \times 10^{-9}$ sec). Emission of energy to the ground state is part of the dualistic nature of fluorescent compounds. Fluorescent compounds show both an excitation and emission spectrum absorbing light during excitation and emitting light of a longer wavelength, (ie. less energetic) light, during emission. This ability to have two readings allows for more accurate and precise readings of compounds than heretofore possible. The spectroscopic reading not being as precise as the fluorescent reading would be aided by having the latter test.

The present invention provides inserts of solid state compounds which intrinsically fluoresce or absorb at a given wave length or have a coating which fluoresces or absorbs at a given wavelength when placed in the reading compartment of a given fluorescence or absorption reader. The inserts are fashioned into the desired shape and are coated by a process which includes baking the coated pieces at 250 degree centigrade for various periods of time (over several days). The coating solutions are chosen to produce various wavelength readings when read upon the coated pieces. Coatings include AgBr, AgCl, Al2O3, BaF2, CaF2, CdTe, CsI, Ge, KBr, KCl, KRS-5, Si, NaCl, Si, SiO2, TiO2, ZnS, ZnSe, HFO2, MgO, Fluroisothiocyanate (FITC), Fluorescene, Rhodamine B, Quinine Sulfate, Bodipy and Green Fluorescent Protein. These coated insert are durable, and provide reliable readings over time (over 3 years). The fluorescence and absorbance readings will not to shift 0.1 OD (Optical Density) in absorbance units and in fluorescence units not more than 1000 fluorescence units within the full scale of 75,000 fluorescence units. The inserts can be fashioned to read at any Optical Density (hereinafter "OD") reading so that a set of inserts with ascending OD units could be used as a concentration curve when read on the appropriate reader.

Furthermore when using a set of solid state standards to calibrate a run, an additional insert with wavelength readings identical to one of the set of calibration standards could be included to check whether the reading one is getting is still within the limits of the assay as described by the calibration curve. Also the insert could be used in UV-visible, Raman, infra-red, and FTIR (fourier transformation infra-red),laser spectroscopy and luminescence spectroscopy. The fluorescence insert can be used as a light source for a luminometer by placing the insert in sunlight for fifteen minutes then immediately placing the insert still in its microplate within the luminometer. The insert will autofluoresce and decay in intensity upon reading in the luminometer. In addition cuvette shaped coated calibration pieces can be used in spectrophotometers and spectrophotometers to calibrate monochromators.

This invention discloses a calibration standard which is unwavering in optical density or relative fluorescence units, stable over time (not changing in reading more than 0.1 Optical Density units in instruments from 0–3.0 Optical Density units or more than 1000 fluorescent units in instruments measuring up to 75,000 Relative Fluorescence units over a 3 year period).

These and other advantages of the present invention will become more thoroughly apparent through the following description of the preferred embodiments and the accompanying drawings.

BRIEF DESCRIPTION OF THE DRAWINGS

A further understanding of the present invention can be obtained by reference to a preferred embodiment set forth in the illustrations of the accompanying drawings. Although the illustrated embodiment is merely exemplary of systems for carrying out the present invention, both the organization and method of operation of the invention, in general, together with As further objectives and advantages thereof, may be more easily understood by reference to the drawings and following description. The drawings are not intended to limit the scope of this invention, which is set forth with particularity in the claims as appended or as subsequently amended, but merely to clarify and exemplify the invention.

For a more complete understanding of the present invention, reference is now made to the following drawings which:

FIG. 1a is a flat bottomed 96 well plate 35 with three vertical and twelve horizontal wells 36. The corresponding inserts 10 and 11 are cylindrically shaped and it shows that they are hatched for ease of identification.

FIG. 1b shows a microplate 35b with a conical bottom with three vertical and twelve horizontally arranged wells. The corresponding inserts 12 and 13, are bullet shaped and are present in duplicate with hatch marks for ease of identification.

FIG. 1c shows a "V" bottomed shaped plate 35c that has a sharp bullet bottom. The corresponding insert 14, has a sharp ended bullet shape and is present in duplicate with hatch marks for ease of identification.

DETAILED DESCRIPTION OF THE INVENTION

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative, yet in regard, they are deemed to afford the best embodiment for purposes of disclosure and to provide a basis for the claims herein which define the scope of the present invention.

The following presents a detailed description of a preferred embodiment of the present invention. As discussed above, the present invention relates generally to fluorescence and absorption spectroscopy using solid state standard coatings on optical glass or quartz. More specifically it relates to the calibration of fluorescence or absorbance reading microplate readers or spectrometers using a solid state device invention which is shaped to fit into square or bullet shaped microplate holders or spectrometer chambers and are read on appropriate fluorescence or absorption readers.

Figures 1A, 1B, 1C:
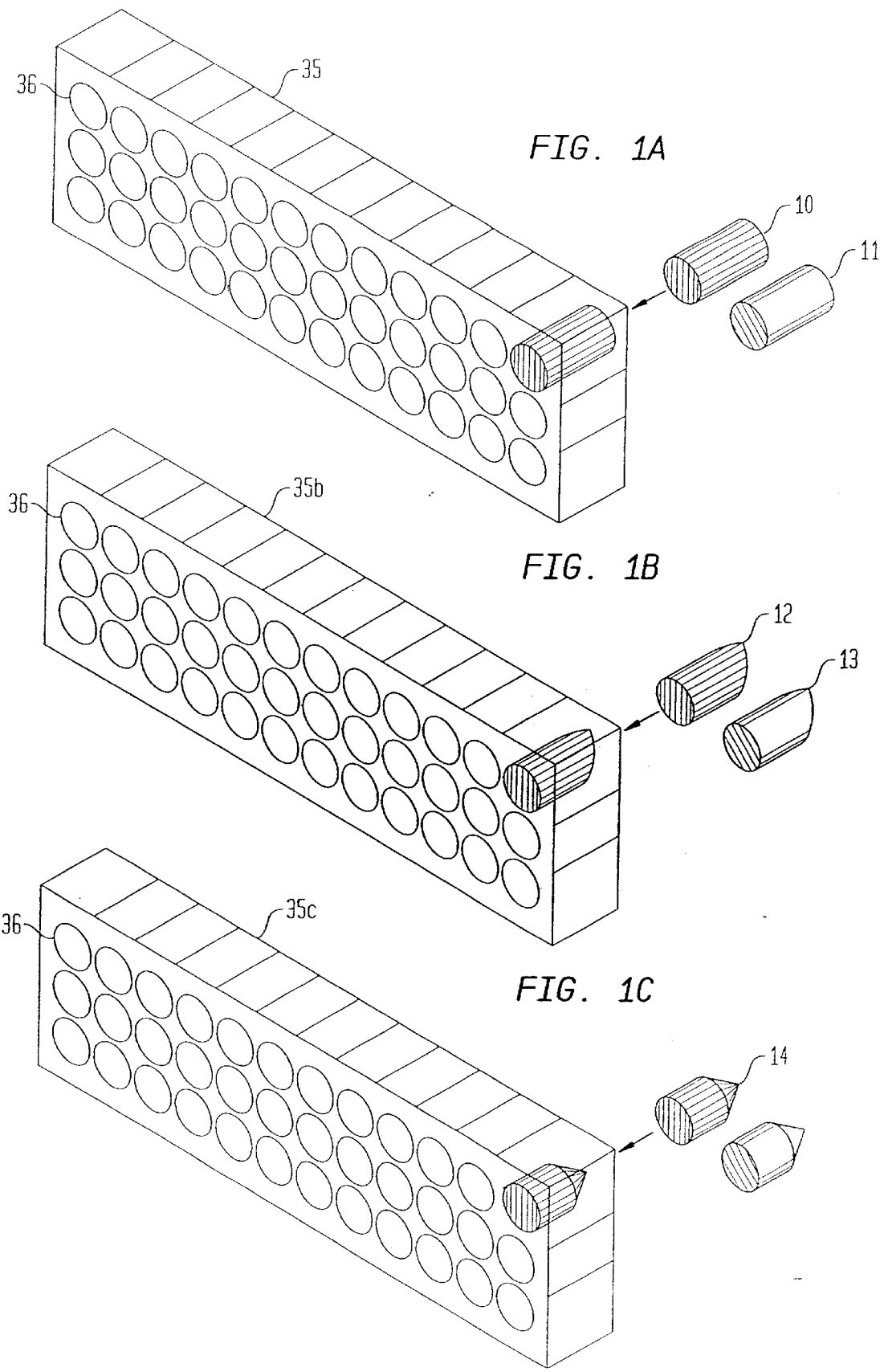
FIGS. 1a–1c is an isometric view of the present invention showing three microplates.

With reference first to FIGS. 1 through 1c which show a microplate in a perspective view. One of the wells 11 is depicted as previously calibrated to show a substance standard having 315–320 nanometers absorption or excitation.

Figure 3:
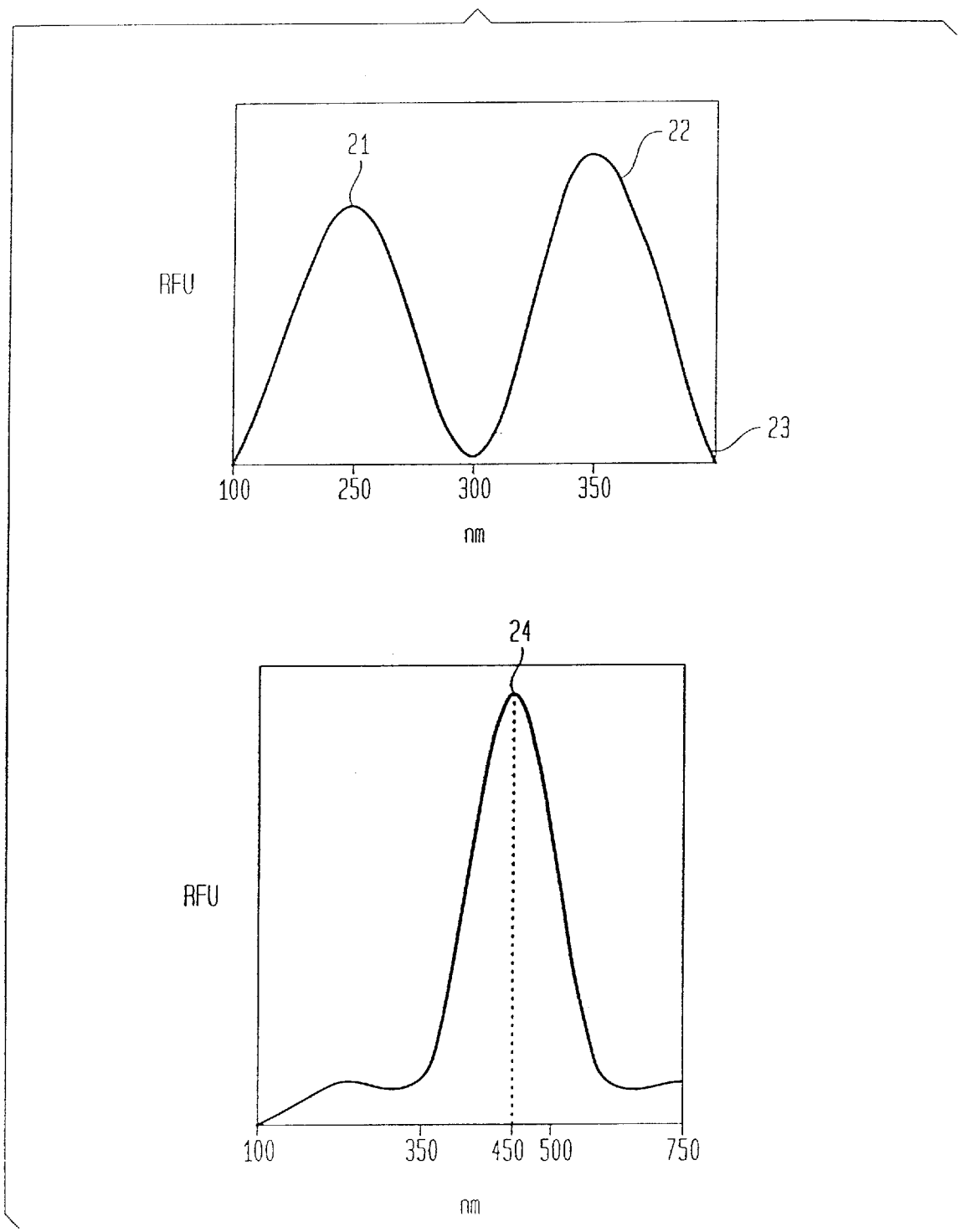
FIG. 3 is a reading of a fluorescent compound showing both dual excitation (absorption) peaks 21 and 22, (in Relative Fluorescence Units-RFU) in the first graph and the single emission curve 24, (RFU) in the other graph.

Turning next to FIG. 3 shown is the absorption and excitation curve plotted in Relative Fluorescent Units (hereinafter "RFU") versus the wavelength of light transmitted in nanometers ("nm"). The curve includes the maximum absorbance 21 and excitation 22 in nanometers, and point 23 represents the end of the excitation with a low RFU value. Peak 24 is the maximum Relative Fluorescent Unit result in the emission phase of the standardization.

Figure 2A:
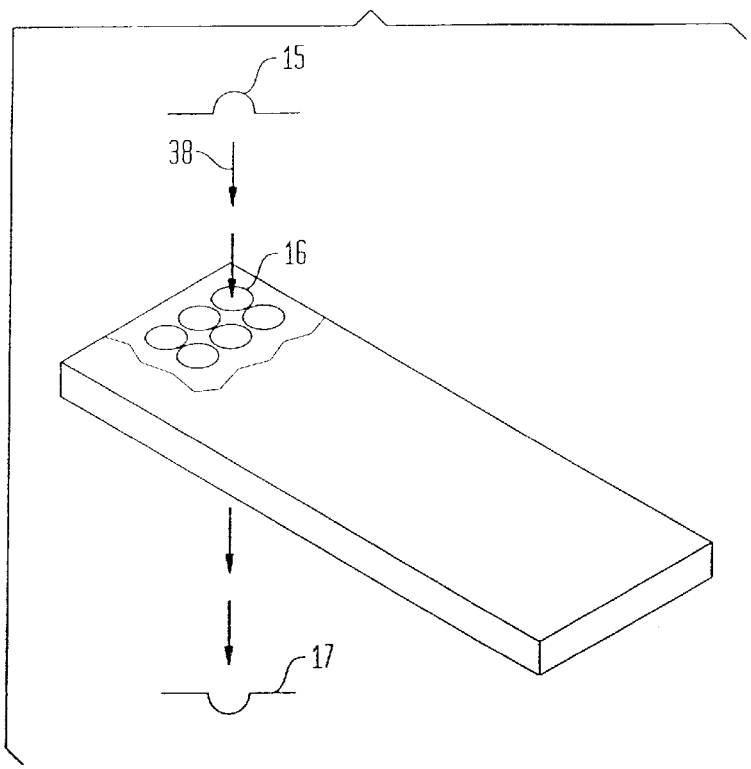
FIG. 2a shows a cylindrical insert 16, oriented in the reading chamber of an absorbance type microplate reader illustrating the transit of light 38 through the insert 16 (from top 15 to bottom 17).
Figure 2B:
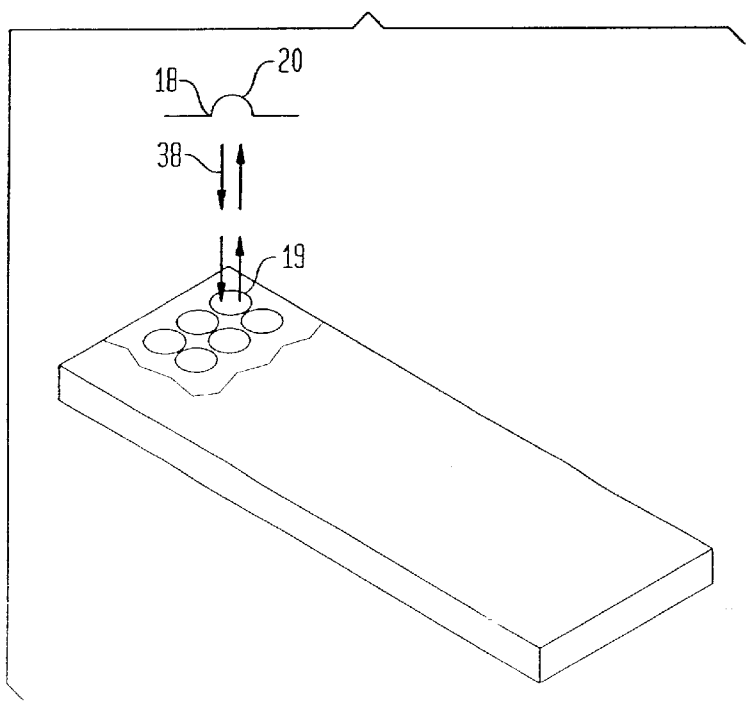
FIG. 2b shows the orientation of the cylindrical insert 19 for fluorescent readers showing excitation light 38 entering the insert from the top 18 and emission light 38 exciting the insert through the same top aperture 20.

In FIG. 2 the solid state standards 16 can be of any geometrical shape (for example see inserts 10, 12 and 14 in FIGS. 1–1c) so long as they permanently show the standard for the compound intended. One embodiment of the present invention uses 96 well plate standards 16 (cylinder or bullet shaped models). This configuration permits solid state measurements in microplates that could be used for reference in microplate readers. The spectroscopic and fluoroscopic measured microplate standards could be solid-state optical glass or quartz with or without known fluorescent, absorbance and spectroscopic compounds. The optical glass itself, with known spectral absorption or fluorescent compounds would be made into solidstate shaped standards that would fit into microplate wells (96) and would be measured in microplate readers. Plate types for holding the solid-state standards would include the 96 well in addition to alternative embodiments of 384, 48, 24, 12, 6 or single well plates. The purpose of the plates 35–35c is to hold these solid-state samples 10–14 in order to give an absorbance or fluorescence standard reading in the corresponding microplate readers. The absorption optical glass standards or the fluorescent glass standards can span wide absorbance range or fluorescence range of from 200–4500 nanometers. This range includes the ultraviolet to the far infra-red.

Figure 4:
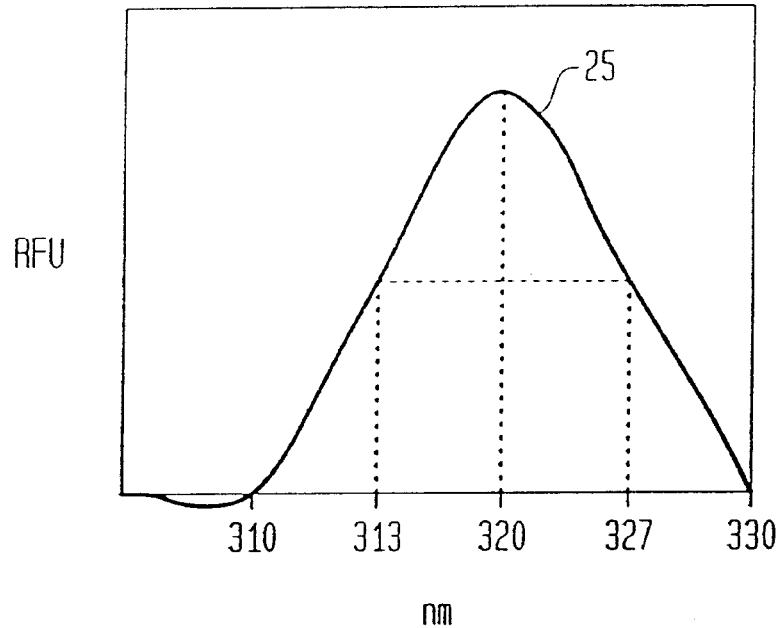
FIG. 4 is the fluorescent excitation 25 and emission 26 of coated optical glass (RFU) vs wavelength (nm). Excitation of the calibration samples 25 and 26 is broad, ranging from 313 nm to 327 nm and 355 nm to 370 nm respectively.
Figure 4:
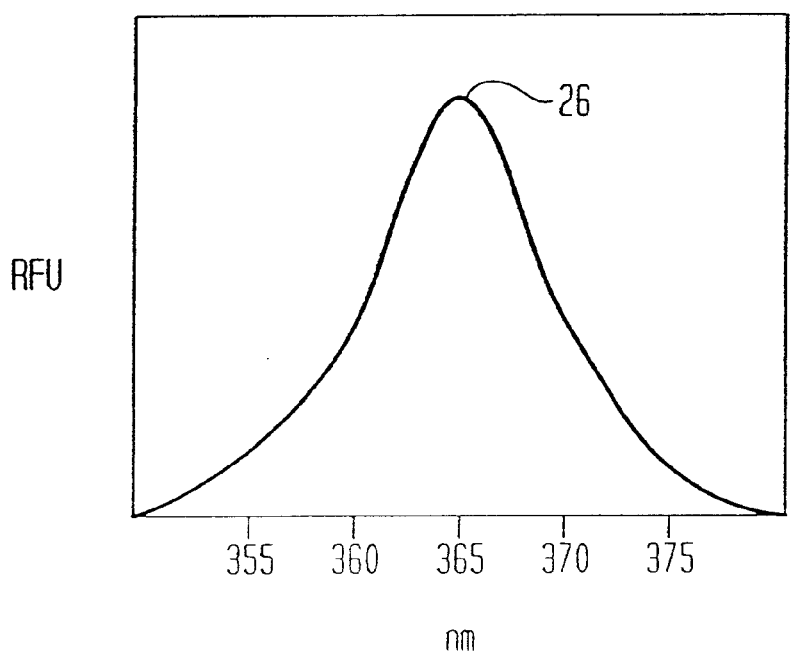

As seen in FIG. 4 one embodiment of the optical glass standard 10–14, operating at a spectroscopic absorption of 320 nanometers, reads at 313 nanometers excitation and 365 nanometers emission. The standards 10–14 could also include different concentrations of the chromophor or fluorophor to be read over a dynamic range, ie, quinine sulfate, a fluorophor, could be coated onto a solid state quartz cylinder and will have a fluorescence emission of 450 nm. These standards 10–14 produce an optical density (absorption for spectroscopic instruments) or fluorometric readings (excitation at 315–320 nm and emission 365–370 nm for optical glass) that can be used to standardize fluorometers. These standard readings would be a way of monitoring instruments for malfunctions in components such as lamps, monochromators, or detector tubes (photomultipliers).

Figure 5:
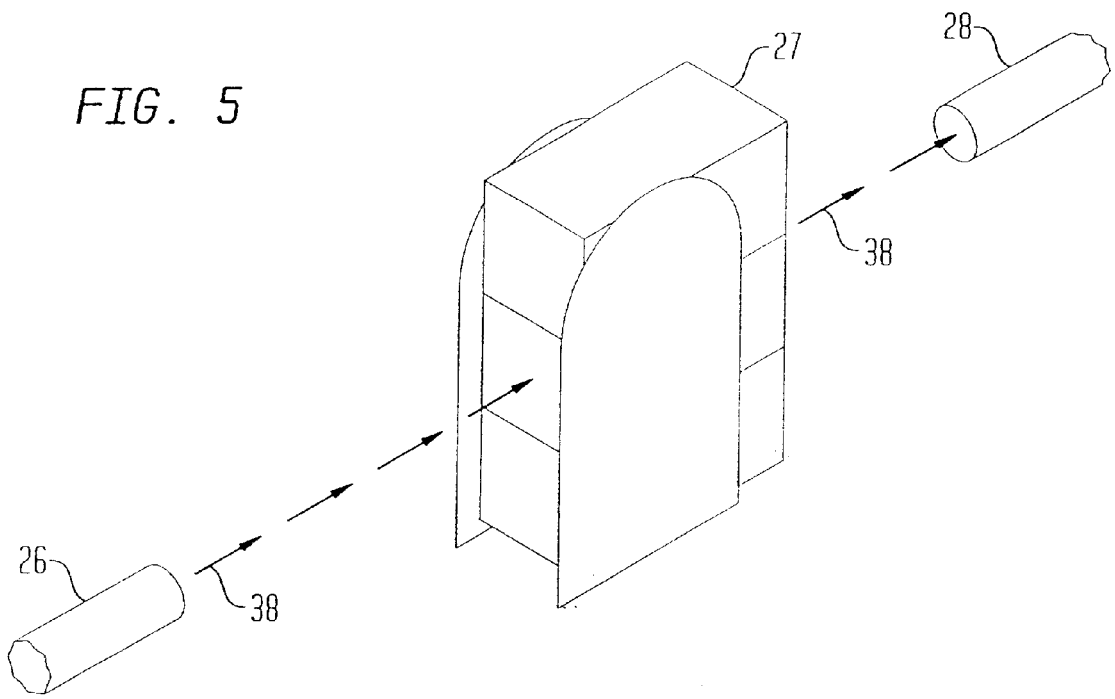
FIG. 5 shows the sample chamber of a spectrophotometer showing a calibration absorption standard cuvette shaped block of coated optical glass 27 and the absorption of light 38 from the it source 26 by the cuvette and transmission of light to photomultiplier tube 28.

FIG. 5 shows the sample chamber of a spectrophotometer where monochromatic light 38 from a source 26, is absorbed by the coated optical glass cuvette 27, and the transmitted light 38 travels to the photodiode 28.

Figure 6:
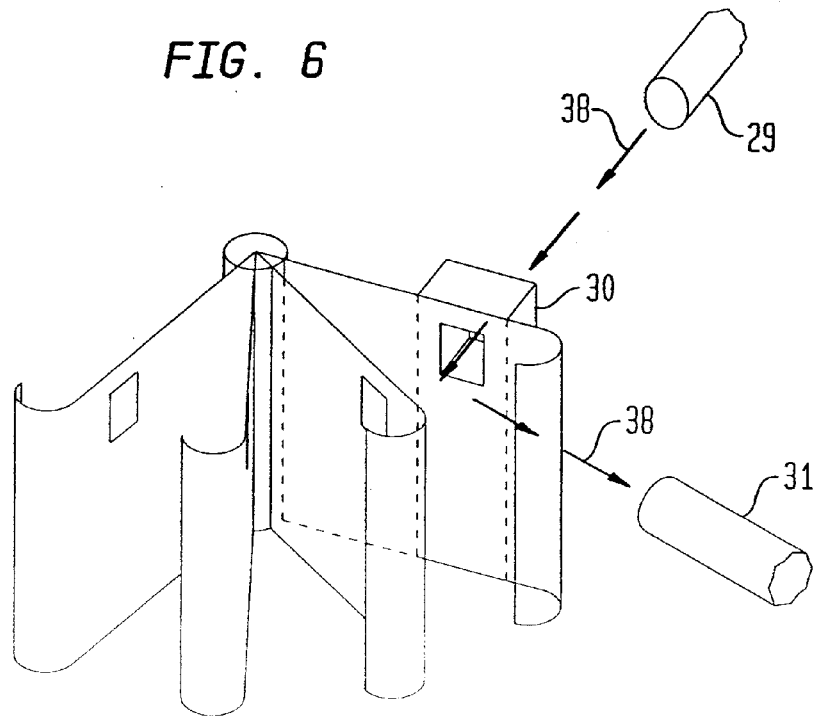
FIG. 6 is the sample chamber of a spectrofluorometer showing a fluorescence coated optical glass cuvette shaped block 30, with excitation light source 29 transmitting light 38 into the cuvette and emission light 38, given off at right angles. The cuvette blocks 30 in FIG. 5 and 6 can be used to calibrate absorbance and fluorescence type instruments.

In FIG. 6 monochromatic excitation light 38 from source 29, excites the coated optical glass cuvette 30 to emit light 38 to be detected by photodiode 31. The optical glass or quartz microplate standards 10–14 will be contoured (shaped to fit into various well plates 35–35c) whether they are round, barrel shaped, square or conical shaped microplate wells. Similarly cuvette shaped coated optical glass could be used in spectrophotometers as seen in FIG. 5, and spectrofluorometers depicted in FIG. 6, to calibrate monochromators.

While the present invention has been described with reference to one or more preferred embodiments, such embodiments are merely exemplary and are not intended to be limiting or represent an exhaustive enumeration of all aspects of the invention. The scope of the invention, therefore shall be defined solely by the following claims. Furthermore, it will be apparent to those of skill in the art that numerous changes may be made in the spirit and the principles of the invention. It should be appreciated that the solid state standard of the present invention is capable of being embodied in other forms without departing from its essential characteristics.

What is claimed is:

1. A solid state standard for spectroscopic readers comprising;
   an excitation source;
   a microplate to orient the solid state standard;
   an optical glass probe, coated with a material with an energy state that can be excited by an external source and which is shaped to fit into said microplate;
   filters for selecting excitation and emissions wavelengths; and
   a detection means integral with said microplate which senses if the reader is operating within pre-determined limits.

2. A solid state standard according to claim 1 wherein said coating material is a fluorescent.

3. A solid state standard according to claim 1 wherein said coating material is a chemical having a known absorption wavelength.

4. A solid state standard according to claim 1 wherein said excitation source is a lamp.

5. A solid state standard according to claim 1 wherein said detection means is a photomultiplier tube.

6. A solid state standard according to claim 1 wherein said detection means is a photodiode array.

7. A method of calibrating a spectroscopic reader with a solid state standard, comprising the steps of:
   shaping a probe to fit into a microplate;
   coating said probe;
   spectroscopic reader will yield a non-fluctuating reading of relative fluorescence units when revolving at a gain of the detection device which is consistent with the peak setting of the instrument;
   using a flourescent compound of known spectral point, generating a calibration curve of incrementally linear varying fluorescence coatings such that each point of the calibration curve represents one coated glass standard; and
   generating a calibration curve to determine if the instrument is operating efficiently at a flourescent point.

8. A method according to claim 7 wherein said probe is coated with a flourescent material.

9. A method according to claim 7 wherein said coating material is a chemical having a known absorption wavelength.

10. A method of calibrating a spectroscopic reader with a solid state standard according to claim 7 wherein said detection device is a photomultiplier tube.

11. A method of calibrating a spectroscopic reader with a solid state standard according to claim 7 wherein said detection device is a photodiode array.

12. A method of calibrating a spectroscopic reader with a solid state standard according to claim 7 wherein said spectroscopic reader is a spectrophotometer monochromator.

13. A method for calibrating a spectrophotometer monochromator comprising the steps of;

coating a cuvette with a material of a known absorbing wavelength;

placing said cuvette in the sample chamber;

scanning said monochromator from zero to its maximum absorbing optical density; and reading the wavelength off said monochromator.

14. A method of calibrating a spectroscopic reader with a solid state standard to determine the maximum excitation and emission wavelength of a flourescent coated glass cuvette, said method comprising the steps of:

placing a flourescent coated glass cuvette with known maximum excitation and emission wavelengths into the chamber;

opening the excitation monochromator to bath the cuvette in white light;

adjusting the emission monochromator from red to violet until a peak is reached;

placing the calibration standard back in the sample chamber and setting the emissions monochromator to its peak value; and scanning the excitation monochromator from red to violet until a maximum reading is determined for the excitation wavelength of the standard.

15. A method of verifying the operational condition of a luminometer, said method consisting of the steps of:

exposing the optical glass pellets of a flat bottomed microplate to direct sunlight; and recording of a peak, in the luminescence reading of the luminomator microplate reader, followed by a decay to background luminescence.

16. A standard according to claim 1, wherein said microplate contains at least one well.

17. A standard according to claim 16, wherein the microplate contains one, six, twelve, twenty-four, forty-eight, ninety-six, three-hundred eighty-four, or fifteen-hundred thirty-six wells.

* * * * *